US009733216B2

(12) United States Patent
Di Lullo et al.

(10) Patent No.: US 9,733,216 B2
(45) Date of Patent: Aug. 15, 2017

(54) APPARATUS AND METHOD FOR MONITORING THE STRUCTURAL INTEGRITY OF A PIPELINE

(71) Applicant: Eni S.p.A., Rome (IT)

(72) Inventors: Alberto Giulio Di Lullo, Tribiano (IT); Giordano Pinarello, Turin (IT); Aldo Canova, Turin (IT)

(73) Assignee: Eni S.p.A., Rome (IT)

( * ) Notice: Subject to any disclaimer, the term of this patent is extended or adjusted under 35 U.S.C. 154(b) by 81 days.

(21) Appl. No.: 14/364,130

(22) PCT Filed: Dec. 20, 2012

(86) PCT No.: PCT/IB2012/057546
§ 371 (c)(1),
(2) Date: Jun. 10, 2014

(87) PCT Pub. No.: WO2013/098728
PCT Pub. Date: Jul. 4, 2013

(65) Prior Publication Data
US 2014/0312887 A1 Oct. 23, 2014

(30) Foreign Application Priority Data

Dec. 30, 2011 (IT) .................................. MI2011A2450

(51) Int. Cl.
*G01N 27/82* (2006.01)
*G01N 27/72* (2006.01)

(52) U.S. Cl.
CPC .................. *G01N 27/82* (2013.01)

(58) Field of Classification Search
CPC .................. G01N 27/82–27/87; G01N 27/902
(Continued)

(56) References Cited

U.S. PATENT DOCUMENTS 3,304,599 A * 2/1967 Nordin ...................... H01F 3/06
174/DIG. 24
3,593,122 A * 7/1971 Barton ..................... G01N 27/90
324/220

(Continued)

FOREIGN PATENT DOCUMENTS

EP 0825435 A1 2/1998
GB 2313644 A * 12/1997 ............ B08B 9/0555
GB WO 2011064603 A1 * 6/2011 .............. F16L 55/28

OTHER PUBLICATIONS

International Search Report dated Feb. 28, 2013 for PCT/IB2012/057546.

(Continued)

*Primary Examiner* — Tung X Nguyen
*Assistant Examiner* — Lee Rodak
(74) *Attorney, Agent, or Firm* — Abel Law Group, LLP

(57) ABSTRACT

An inspection apparatus (100) for monitoring the structural integrity of a pipeline (101) comprising a central electromagnetic device (102) suitable for generating a magnetic field (106); a pair of magnetic conveyors (103', 103") connected to the central electromagnetic device (102) suitable for conveying the magnetic field (106) to the wall of the pipeline (101); a system of sensors (104) for revealing the magnetic field (106) conveyed on the pipeline (101); electric means (105) for feeding the inspection apparatus (100) and acquiring and storing data relating to the magnetic field (106) revealed; wherein said central electromagnetic device (102) is divided into various ferromagnetic elements (107) held together by a casing (109) made of polymeric material suitable for degrading after prolonged contact with a mixture of hydrocarbons. Method wherein an inspection apparatus according to the present invention is used for monitoring the structural integrity of a pipeline (101).

18 Claims, 2 Drawing Sheets

(58) Field of Classification Search
USPC ........ 324/228–231, 219–222; 73/152.54, 86, 73/104, 865.8
See application file for complete search history.

(56) References Cited

U.S. PATENT DOCUMENTS

| | | | |
|---|---|---|---|
| 4,072,894 A | | 2/1978 | Barton |
| 4,447,777 A * | | 5/1984 | Sharp ..................... G01N 27/82 |
| | | | 324/220 |
| 4,769,598 A * | | 9/1988 | Krieg ................ G01N 29/2412 |
| | | | 324/219 |
| 5,454,276 A * | | 10/1995 | Wernicke ........... G01N 27/9013 |
| | | | 324/220 |
| 5,546,065 A * | | 8/1996 | Vinciarelli ............ H01F 27/346 |
| | | | 336/212 |
| 6,009,756 A * | | 1/2000 | Willems ............... G01N 27/902 |
| | | | 73/592 |
| 6,190,090 B1 * | | 2/2001 | Campbell ............ B08B 9/0551 |
| | | | 15/104.061 |
| 6,232,773 B1 | | 5/2001 | Jacobs et al. |
| 6,384,738 B1 * | | 5/2002 | Carstensen ............. E21B 34/06 |
| | | | 340/853.1 |
| 7,859,256 B1 | | 12/2010 | Hoyt et al. |
| 2004/0040389 A1 * | | 3/2004 | Buttle ..................... G01L 1/127 |
| | | | 73/862.046 |
| 2004/0183528 A1 * | | 9/2004 | Crouch ................ G01N 27/725 |
| | | | 324/220 |
| 2008/0173109 A1 * | | 7/2008 | Cogen ..................... F16L 55/26 |
| | | | 73/865.8 |
| 2009/0107684 A1 * | | 4/2009 | Cooke, Jr. ............... E21B 23/00 |
| | | | 166/376 |
| 2014/0374106 A1 * | | 12/2014 | Zhu ......................... D01D 5/30 |
| | | | 166/305.1 |

OTHER PUBLICATIONS

"QPP_Catalogue_2009", Jan. 1, 2009, Retrieved from the Internet: URL:http://www.qualitypollypig.com/QPP_Catalogue_2009.pdf.

* cited by examiner

APPARATUS AND METHOD FOR MONITORING THE STRUCTURAL INTEGRITY OF A PIPELINE

The present invention relates to an inspection apparatus, and the relative method, for determining the structural integrity of a pipeline made of a metallic material.

More specifically, the present invention relates to an inspection apparatus for monitoring the structural integrity of a pipeline, whether it be offshore or onshore, using an inspection device for pipelines, commonly known as "pipeline inspection gauge" or "pig".

There are various methods for inspecting the conditions of a pipeline. These methods normally adopt means known in the art as "pigs" or "foam pigs", the latter being produced in polymeric foam.

Said "pigs" or "foam pigs" are generally in cylindrical form, spherical or bullet-shaped, and are launched or passed into a pipeline for a certain length of the same.

The simplest versions are used for cleaning pipelines, whereas the more advanced versions equipped with electronics and instrumentation onboard, allow various types of measurements and surveys.

An evaluation of the integrity of a pipeline is a fundamental aspect, above all in the oil industry. Possible damage or significant anomalies to the walls of the pipeline can in fact make it unsafe and consequently unusable.

Pipelines carrying gas, petroleum or other oil industry products can be subject to damage due to various factors, such as, for example, mechanical stress, impact or chemical and electrolytic action of the substances contained therein.

In particular, the thinning of the thickness of a wall of a pipeline in certain points can, with time, lead to ruptures.

Systems for verifying the integrity of a metallic pipeline using magneto-inductive techniques are known in the state of the art.

It is also known that the thinning of the walls of a pipeline causes a variation in the flow of the magnetic field induced in the same. Said magneto-inductive techniques are in fact capable of revealing variations in the thickness of the wall of the pipeline, due for example to thinning or another type of damage.

In these magneto-inductive techniques, a system that is situated inside the pipeline induces a magnetic field in the ferromagnetic wall of the pipeline and simultaneously performs measurements on the magnetic field induced. In particular, the use of these systems installed in devices for the inspection of pipelines or "pigs" is known in the state of the art.

U.S. Pat. No. 4,072,894, for example, describes an apparatus for non-destructive inspections of pipelines comprising a device capable of generating a magnetic field, spatulas suitable for carrying the magnetic field inside the wall of the pipeline and means for revealing magnetic field losses due to possible thinning or damage to the wall of the pipeline.

The apparatus described in the above patent is extremely bulky and mechanically rigid, and requires a previous cleaning of the pipeline to be able to operate and avoid operating risks to the same. In the case of blockage of the apparatus inside the pipeline, due to a narrowing or partial obstruction of the same, the recovery operation of the apparatus requires a considerable operational and consequently economic effort: the more extensive the apparatus, the more difficult it is to recover it from the pipeline in the case of blockage.

Although the apparatus described in the above U.S. Pat. No. 4,072,894 allows possible stress points of the pipeline to be detected, the Applicant has found that it is not without drawbacks and can be improved in various aspects, mainly with respect to the fact that a possible blockage of the apparatus in the pipeline can lead to the temporary non-use of the same. In particular, in the case of a pipeline carrying hydrocarbons, an interruption in the transportation can cause huge economic losses and operational problems for all the phases downstream of the interruption.

In the state of the art, there are also devices or "pigs" equipped with permanent magnets, rather than electromagnets. In this type of apparatus, the magnetic field is generated without the use of electric current.

The Applicant has found however that "pigs" having permanent magnets are extremely heavy due to the magnets and consequently the passage of the "pig" in the pipeline is slower and increases the risk of blockage in the same.

Furthermore, in the case of breakage of the apparatus, the permanent magnet forms a rigid block which, when carried by the fluid flowing in the pipeline, can represent a danger for the integrity of the pipeline itself.

In conclusion, with the "pigs" having magneto-inductive systems currently known, it is not possible to effect surveys on the conditions of the walls of the pipeline, minimizing operational risks and avoiding a preventive cleaning of the pipeline.

An objective of the present invention is to overcome the drawbacks indicated above and in particular to conceive an inspection apparatus for monitoring the integrity of a pipeline that minimizes risks of damage to the pipeline itself and the elements present therein, in particular the valves.

A further objective of the present invention is to provide an inspection apparatus which, in the case of blockage, does not interrupt the flow passing through the pipeline, and, in the case of breakage, is easy to recover, for example by means of a "foam pig".

Another objective of the present invention is to provide an inspection apparatus for monitoring the integrity of a pipeline which does not require previous cleaning of the same to be deployed.

These and other objectives according to the present invention are achieved by providing an inspection apparatus for monitoring the structural integrity of a pipeline as specified in claim 1.

Further characteristics of the inspection apparatus for monitoring the structural integrity of a pipeline are object of the dependent claims.

The characteristics and advantages of the inspection apparatus for monitoring the structural integrity of a pipeline according to the present invention will appear more evident from the following illustrative and non-limiting description, referring to the enclosed schematic drawings, in which.

Figure 1:
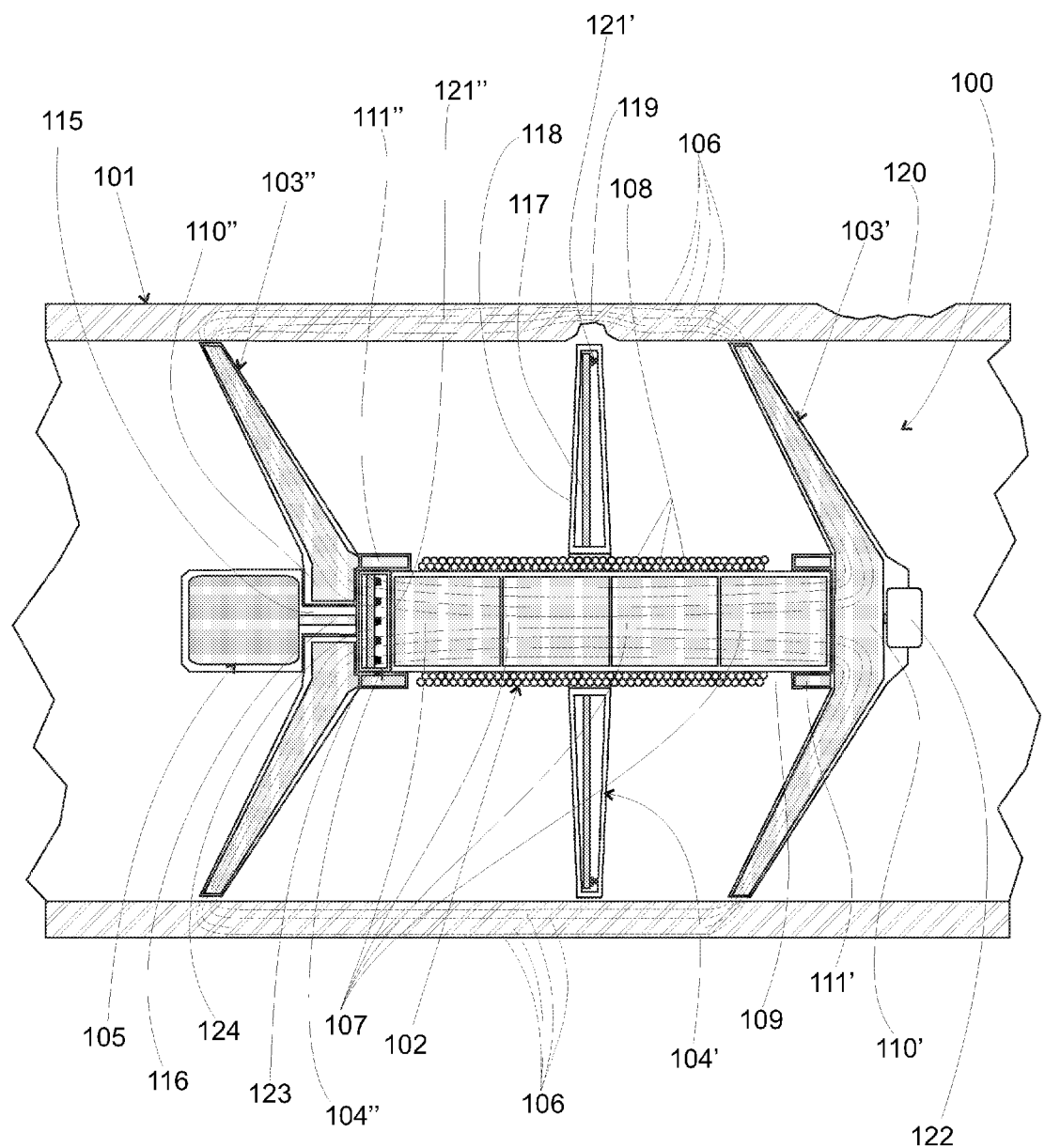
FIG. 1 is a schematic sectional view of a preferred embodiment of an inspection apparatus of a pipeline for monitoring the structural integrity of a pipeline.

With reference to FIG. 1, it is shown an inspection apparatus of a pipeline, indicated as a whole with 100, for monitoring the structural integrity of a pipeline 101.

The inspection apparatus 100 of a pipeline 101 comprises:
a central electromagnetic device 102 which extends longitudinally in the pipeline 101, suitable for generating a magnetic field 106;
a first magnetic conveyor 103' connected to an end of the central electromagnetic device 102 suitable for conveying the magnetic field 106 generated by the central electromagnetic device 102 to the wall of the pipeline 101;

a second magnetic conveyor 103" connected to the opposite end of the central electromagnetic device 102, with respect to the first magnetic conveyor 103', suitable for facilitating the closing of a magnetic circuit, conveying the magnetic field 106 from the wall of the pipeline 101 towards the central electromagnetic device 102;

at least one sensor system 104 for revealing the magnetic field 106 present at the wall of the pipeline 101;

electric means 105 connected to the central electromagnetic device 102, for powering the inspection apparatus 100 and acquiring and storing data relating to the magnetic field 106 revealed.

Said inspection apparatus 100 of a pipeline 101 is an apparatus suitable for being inserted in a pipeline 101 and more generally falls within the group of "pipeline inspection gauges".

Said central electromagnetic device 102, having a substantially cylindrical form, is divided into various elements 107 positioned adjacently and made of a ferromagnetic material, preferably an iron-cobalt alloy, held together by a casing 109 made of polymeric material suitable for degrading following prolonged contact with a mixture of hydrocarbons.

Thanks to this solution, if the inspection apparatus remains stuck in the pipeline 101, the casing 109 made of polymeric material dissolves, releasing the various elements 107 of the central electromagnetic device 102. In this way, the central electromagnetic device 102 breaks up into a multitude of pieces having reduced dimensions which are no longer dangerous for the pipeline 101.

These elements 107 are enveloped by a solenoid 108. When said solenoid 108 is subjected to an electric current, it generates a magnetic field 106 which passes through the elements 107 longitudinally.

In particular, said elements 107 can have such a shape and dimension that they do not represent a risk for the pipeline 101. Said elements 107, for example, can have a cylindrical or spherical shape to allow them to roll more easily in the pipeline 101 in the case of breakage of the inspection apparatus 100.

Said first and second magnetic conveyor 103', 103", hereinafter indicated for the sake of simplicity with the term magnetic conveyors, are both made of a flexible polymeric material suitable for degrading into small-sized elements following prolonged contact with a mixture of hydrocarbons. Said first magnetic conveyor 103' and said second magnetic conveyor 103" comprise a flexible core made of ferromagnetic material 110', 110", in their interior.

In a preferred embodiment, said magnetic conveyors 103', 103" transversally have a disc or daisy form, and longitudinally an arched shape which takes into account the advance movement of the device, facilitating its passing through the pipeline 101.

Said arched shape also guarantees a constant adhesion of the magnetic conveyors 103', 103" to the internal wall of the pipeline 101, thanks to the elastic thrust that the magnetic conveyors 103', 103" exert on the internal wall of the pipeline 101, once the inspection apparatus 100 has been inserted in the same.

In a preferred embodiment, the flexible core made of ferromagnetic material 110', 110" of the magnetic conveyors 103', 103" consists of a bundle or pack of steel wires, preferably made of an alloy having a low magnetic saturation, in which the diameter of each wire is less than 0.5 mm and wherein the magnetic permeability of the wire preferably ranges from 1500 to 2000 H/m.

The flexibility of the magnetic conveyors 103', 103" allows the inspection apparatus 100 to pass over any possible section changes of the pipeline 101, due to defects of the same, accumulation areas, deposits, or valves.

In a particular version of the present invention, said magnetic conveyors 103', 103" can have a multilayer structure for improving the magnetic conductivity. In this particular embodiment, said first magnetic conveyor 103' and said second magnetic conveyor 103" can be composed of various discs (not illustrated) made of polymeric material, each having a core made of ferromagnetic material.

In a particular embodiment of the present invention, said magnetic conveyors 103', 103" can comprise a metallic ring 111', 111" at least partly enveloping the central electromagnetic device 102 in correspondence with the connection between the central electromagnetic device 102 and the magnetic conveyors 103', 103", with the function of reducing leakages of the magnetic field lines 106.

In general, said magnetic conveyors 103', 103" optimize the maintenance of the magnetic flux and limit the gap between the end of the magnetic conveyors 103', 103" and the internal wall of the pipeline 101.

In a preferred embodiment of the present invention, said system of sensors 104 can be of the LF type 104' (localized fault) or LMA type 104" (loss of metal cross-section area) type.

Said sensor system of the LF type 104' can comprise magnetic sensors 121', suitable for detecting the magnetic field 106, connected to a flexible support 117 made of polymeric material.

Said flexible support 117 of said sensor system of the LF type 104' can have, transversally, a circular shape or a circular-crown, having an external diameter close to the internal diameter of the pipeline 101, and can be positioned orthogonally with respect to the central electromagnetic device 102.

Said magnetic sensors 121' are arranged in a circular configuration substantially along the edge of the flexible support 117, so as to be positioned close to the internal wall of the pipeline 101.

The proximity of said magnetic sensors 121' to the internal wall of the pipeline 101, allows the sensor system of the LF type 104' to reveal local variations in the magnetic field 106, in particular the radial component, close to the wall of the pipeline 101. This type of detection allows useful information to be obtained on the presence and angular position of defects having reduced dimensions 119.

Said sensor system of the LF type 104' can comprise a flexible casing 118 suitable for containing said flexible support 117 and said magnetic sensors 121'. Said flexible casing 118 can be connected to said central electromagnetic device 102 orthogonally and extend from this until it touches the internal wall of the pipeline 101.

The flexibility of the flexible casing 118 combined with the flexibility of the flexible support 117 allow the inspection apparatus 100 to pass over any possible deposits or deformations present in the pipeline 101.

Said sensor system of the LMA type 104" can comprise magnetic sensors 121", suitable for detecting the magnetic field 106, connected to a support 124.

Said sensor system of the LMA type 104" can be positioned coaxially with respect to the central electromagnetic device 102 and have an essentially circular shape.

The coaxial arrangement of the system of sensors of the LMA type 104" allows extensive corrosion phenomena 120 to be revealed, through measuring the total axial magnetic field 106 that passes through the magnetic sensors 121".

Said sensor system of the LMA type 104" can be interposed between one of the magnetic conveyors 103', 103" and said central electromagnetic device 102.

Furthermore, said sensor system of the LMA type 104" can comprise a protective shell 123 suitable for protecting and containing the support 124 and magnetic sensors 121" connected to it.

Said flexible casing 118 and said protective shell 123 can be made of a polymeric material suitable for degrading after prolonged contact with a mixture of hydrocarbons.

Said inspection apparatus 100 can simultaneously comprise said system of sensors of the LF type 104' and said system of sensors of the LMA type 104" or, alternatively, only one of the two.

In a preferred embodiment of the present invention, said inspection apparatus 100 also comprises a spatial localization system 122 suitable for revealing the positioning of the inspection apparatus 100.

Said spatial localization system 122 comprises a clock (not illustrated) for obtaining a time reference which is associated with at least one position variation measurement, obtained by means of at least one of the following instruments:
- a gyroscope (not illustrated), for determining the inclination of the inspection apparatus 100;
- an accelerometer (not illustrated) for measuring the acceleration of the inspection apparatus 100 and consequently its variations in velocity;
- a pressure sensor (not illustrated) for revealing the variations in pressure to which the inspection apparatus 100 is subjected, useful for understanding whether the apparatus 100 has passed over possible section changes of the pipeline 101, such as for example welds or valves, having prefixed positions in the pipeline 101.

By associating the data revealed by the sensor system 104 relating to the magnetic field 106, with the data relating to the time reference and position obtained by the localization system 122, it is possible to localize the structural imperfections present on the walls of the pipeline 101.

In a preferred embodiment of the present invention, said electric means 105 can comprise at least one battery (not illustrated), preferably with lithium ions, at least one acquisition system (not illustrated) and the relative electric connection means (not illustrated) to the central electromagnetic device 102, the sensor system 104 and localization system 122.

Said battery is dimensioned so as to guarantee an electric charge sufficient for supplying the central electromagnetic device 102 for a time longer than or equal to 1.2 times the expected duration of the monitoring mission, and in any case for a time not longer than 72 hours, preferably less than 12 hours.

In the case of blockage of the inspection apparatus 100 in the pipeline 101, the short duration of the battery allows the magnetic effect of the same to become exhausted in a few hours, thus preventing the magnetic effect from causing the inspection apparatus 100 to adhere to a wall of the pipeline, making its recovery more difficult.

Said acquisition system comprises a measurement card (not illustrated), suitable for processing the data relating to the magnetic field 106 detected by the sensor system 104 and the time and position data obtained by the spatial localization system 122, and a storage system (not illustrated) of the detected data.

In particular, said magnetic sensors 121', 121" allow variations in the magnetic field 106 to be revealed, whereas said measurement cards process the signal detected.

In a preferred embodiment of the present invention, said electric means 105 are connected to the central electromagnetic device 102 by means of a connector 115 made of polymeric material suitable for degrading after prolonged contact with a mixture of hydrocarbons. Said connector 115 also comprises conductor means 116 for the passage of data and power.

In a particular version of the present invention, said electric means 105 can be outside the inspection apparatus 100, and, in particular, contained in a pig (not illustrated) independent of the inspection apparatus 100, connected to it by means of a flexible connection system (not illustrated), possibly made of polymeric material suitable for degrading after prolonged contact with a mixture of hydrocarbons.

Figure 2:
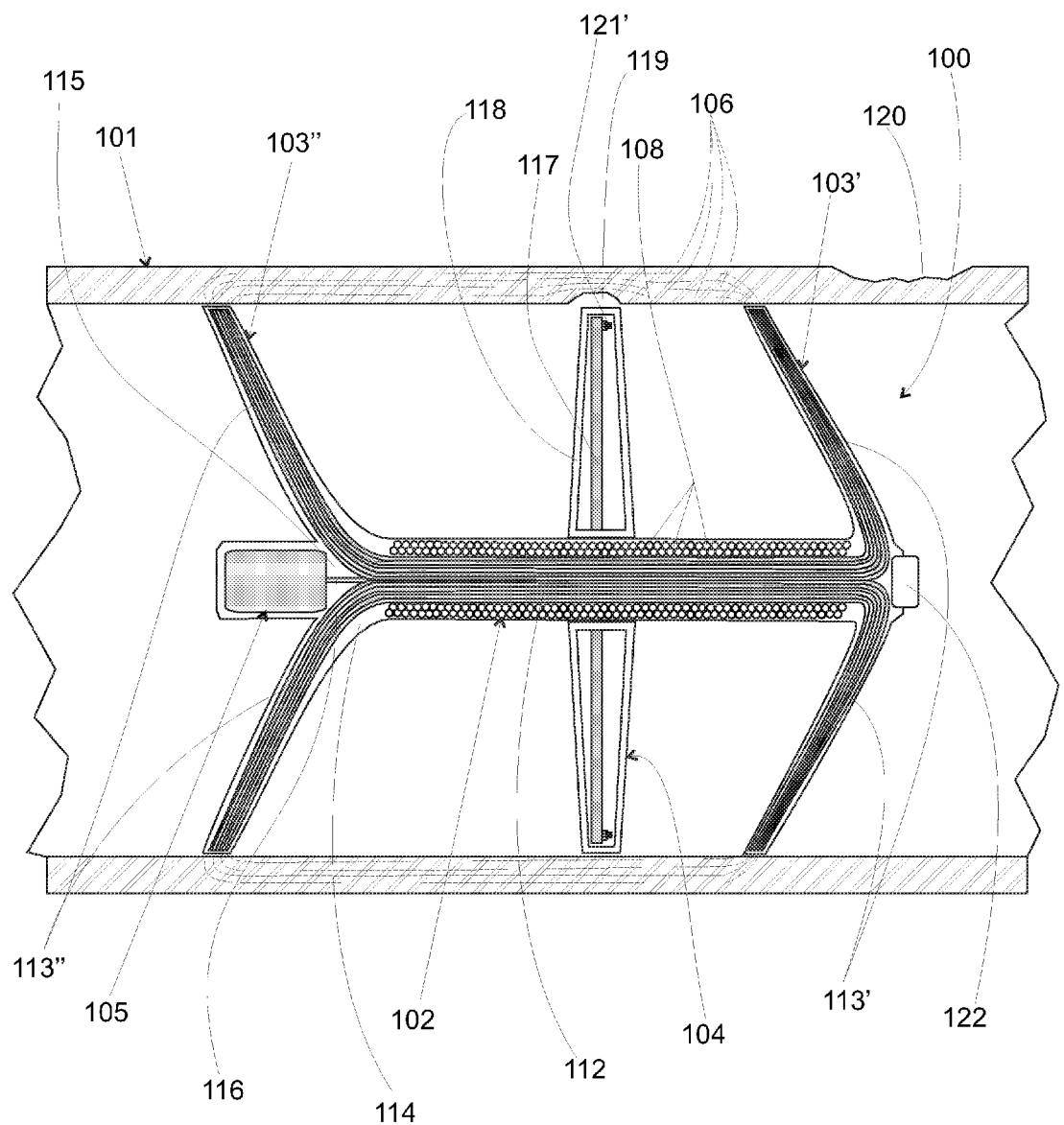
FIG. 2 is a schematic sectional view of an alternative embodiment of an inspection apparatus of a pipeline for monitoring the structural integrity of a pipeline.

With reference to FIG. 2, this shows a particular embodiment of the inspection apparatus 100 (the same reference numbers have the same meaning indicated in FIG. 1), wherein said first and second magnetic conveyor 103', 103" are integral with the central electromagnetic device 102.

In particular, the central electromagnetic device 102 can comprise a bundle of metallic wires 112 which opens at the two ends into multiple sub-bundles of wires 113', 113". Said sub-bundles of wires 113', 113" are included in said first and second magnetic conveyors 103', 103" and extend until they touch the internal wall of the pipeline 101.

Said bundle of metallic wires 112 is enveloped in its central part by a solenoid 108 which, when traversed by electric current, generates a magnetic field 106 (indicated in FIG. 2 with a dashed line) which passes through said bundle of wires 112 and said sub-bundles of wires 113', 113" until it reaches the internal wall of the pipeline 101.

Said bundle of metallic wires 112, said sub-bundles of wires 113', 113" and said solenoid 108 are contained in a sheath made of polymeric material 114, suitable for degrading following prolonged contact with a mixture of hydrocarbons, which holds them together.

Said sub-bundles of wires 113', 113" convey the magnetic field 106 towards the pipeline 101, and, transversally, can have a daisy-shaped configuration.

According to the present invention, said polymeric material, contained in the casing 109, in the first and second magnetic conveyor 103', 103", in the sheath 114, in the connector 115, in the flexible casing 118 and in the protective shell 123, is a polymeric material suitable for degrading following prolonged contact with a mixture of hydrocarbons, due to the chemical aggression of the hydrocarbons and mechanical action of the fluid flowing in the pipeline.

In particular, said polymeric material satisfies at least one of the following characteristics:
- glass transition temperature lower than the typical temperature range of use in the inspection apparatus 100, preferably lower than 10° C.,
- melting point higher than the typical temperature range of use in the inspection apparatus 100, preferably higher than 70° C.

In particular, said polymeric material can be ethylene vinyl acetate (EVA). This material corresponds to the characteristics indicated above and degrades in a few days into small-sized pieces if attacked by a hydrocarbon mixture.

A further object of the present invention relates to a method for monitoring the structural integrity of a pipeline 101 comprising the phases described hereunder.

As said inspection apparatus 100 does not have its own propelling means, it moves along the pipeline 101 thanks to a thrust exerted by the fluid flowing in the same pipeline.

Once inserted in the pipeline 101, the inspection apparatus 100 begins its monitoring operation that lasts until it reaches the receiving trap (not illustrated), in which the inspection apparatus 100 enters once it has completed its monitoring intervention.

During its monitoring operation, the inspection apparatus 100 generates a magnetic field 106 which is conveyed to the wall of the pipeline 101 by the magnetic conveyors 103', 103" and revealed by the sensor system 104.

In particular, the sensor system 104 reveals the variations in the magnetic field 106 that can indicate any possible reduction areas of the thickness of the wall of the pipeline 101.

A variation of the magnetic field 106 to the wall of the pipeline 101 can indicate a reduction in the thickness of the wall of the pipeline 101 or an imperfection of the same.

These data measured by the sensor system 104 are stored by electric means 105 together with the data relating to the position obtained by the spatial localization system 122 of the inspection apparatus 100, and can be recovered by the same once the monitoring operation has been completed.

An analysis of the data recovered by the inspection apparatus 100 can provide useful indications with respect to possible structural imperfections 119, 120 present on the walls of the pipeline 101.

Said inspection apparatus for monitoring the structural integrity of a pipeline, object of the present invention, is particularly suitable for use in pipelines destined for the transportation of hydrocarbons.

The characteristics of the apparatus and method for monitoring the structural integrity of a pipeline, object of the present invention, are evident from the description, as also the relative advantages.

In particular, one of the advantages of the apparatus and method according to the present invention is to allow the localization of possible structural imperfections or anomalies of the walls of a pipeline without jeopardizing the safety of the pipeline itself.

In the case of blockage in the pipeline, the inspection apparatus according to the present invention is, in fact, capable of breaking up into multiple light components, having small dimensions and not dangerous for the pipeline.

The structure of the inspection apparatus is conceived so as to disintegrate into numerous pieces within a few days.

After prolonged contact of the inspection apparatus with a mixture of hydrocarbons, the components made of polymeric material degrade and dissolve in the hydrocarbon mixture, releasing the parts connected to them.

These released parts, generally metallic or in any case not dissolvable in the hydrocarbon mixture, are designed to minimize the risk of damage to the pipeline. The weight and dimensions of these non-dissolvable parts are such that they do not represent a risk for the integrity of the pipeline nor a hindrance or risk for possible subsequent monitoring operations effected with any type of known pig.

A further advantage of the inspection apparatus according to the present invention is represented by the fact that the flexible structure of the same allows the inspection apparatus to be utilized for the monitoring of pipelines that have not been previously cleaned of deposits of waxes, paraffins, asphaltenes or sand.

Thanks to its structural flexibility, the inspection apparatus is in fact capable of passing over obstacles and/or partial obstructions present in the pipeline without remaining embedded.

The inspection apparatus is also suitable for being used in pipelines having a small diameter, preferably with a diameter starting from 3 inches.

The apparatus and method for monitoring the structural integrity of a pipeline of the present invention thus conceived, can, in any case, undergo several modifications and variants, all included in the same inventive concept. The protection range of the invention is therefore defined by the enclosed claims.

The invention claimed is:

1. A pipeline inspection gauge for monitoring the structural integrity of a pipeline, the pipeline inspection gauge being adapted to be inserted in a pipeline and to move along the pipeline, wherein the pipeline inspection gauge is adapted, during a monitoring operation, to generate a magnetic field which is conveyed to the wall of the pipeline and to reveal variations in the magnetic field using a sensor system, the pipeline inspection gauge comprising:
   a central electromagnetic device adapted to generate a magnetic field;
   a first magnetic conveyor connected to said central electromagnetic device suitable for conveying the magnetic field generated by the central electromagnetic device to the wall of the pipeline;
   a second magnetic conveyor connected to said central electromagnetic device suitable for facilitating the closing of a magnetic circuit, conveying the magnetic field from the wall of the pipeline towards the central electromagnetic device;
   at least one sensor system for revealing the magnetic field;
   electric means for powering the pipeline inspection gauge and acquiring and storing data relating to the magnetic field detected;
wherein said central electromagnetic device includes a plurality of divided elements made of a ferromagnetic material that are each a smaller size than said central electromagnetic device, wherein said divided elements are held together by a polymeric material adapted to degrade following prolonged contact with a mixture of hydrocarbons which results in separation of said divided elements and loss of the generated magnetic field; and
a solenoid that envelops said divided elements which, when subjected to an electric current, generates the magnetic field which passes through said divided elements longitudinally.

2. The pipeline inspection gauge according to claim 1, wherein said first and second magnetic conveyor are made of a flexible polymeric material suitable for degrading following prolonged contact with a mixture of hydrocarbons and comprise a flexible core made of ferromagnetic material, in their interior.

3. The pipeline inspection gauge according to claim 2, wherein said flexible core made of ferromagnetic material consists of a bundle or pack of steel wires.

4. The pipeline inspection gauge according to claim 1, wherein said first and second magnetic conveyor comprise a metallic ring at least partly enveloping the central electromagnetic device at the connection between the central electromagnetic device and said first and second magnetic conveyor, with the function of reducing the exiting of the magnetic field lines.

5. The pipeline inspection gauge according to claim 1, wherein said sensor system is of the localized fault type or loss of metal cross-section area type.

6. The pipeline inspection gauge according to claim 5, wherein said sensor system of the localized fault type, suitable for revealing local variations in the magnetic field close to the wall of the pipeline, comprises magnetic sensors, connected to a flexible support and arranged in a circular configuration substantially along the edge of the flexible support.

7. The pipeline inspection gauge according to claim 5, wherein said sensor system of the loss of metal cross-section area type, suitable for measuring the total axial magnetic field, positioned coaxially with respect to the central electromagnetic device, comprises magnetic sensors connected to a support.

8. The pipeline inspection gauge according to claim 1, comprising a spatial localization system suitable for revealing the positioning of the pipeline inspection gauge.

9. The pipeline inspection gauge according to claim 1, wherein said electric means comprise at least one battery and at least one acquisition system.

10. The pipeline inspection gauge according to claim 9, wherein said battery guarantees an electric charge sufficient for powering the central electromagnetic device for a time not longer than 72 hours.

11. The pipeline inspection gauge according to claim 9, comprising a spatial localization system suitable for revealing the positioning of the pipeline inspection gauge, wherein said acquisition system comprises a measurement card, suitable for processing the data relating to the magnetic field revealed by the sensor system and the position data obtained by the spatial localization system, and a storage system of the data revealed.

12. The pipeline inspection gauge according to claim 1, wherein said polymeric material is ethylene vinyl acetate.

13. A method for monitoring the structural integrity of a pipeline which comprises the following phases:
providing a pipeline inspection gauge according to claim 1;
inserting said pipeline inspection gauge into the pipeline for a monitoring operation;
generating a magnetic field by means of said pipeline inspection gauge, which is conveyed to the wall of the pipeline;
revealing, by means of said pipeline inspection gauge, the variations in the magnetic field conveyed to the wall of the pipeline;
storing said data relating to the variations in the magnetic field in the pipeline inspection gauge;
recovering said data relating to the variations in the magnetic field from the pipeline inspection gauge;
analyzing said data relating to the variations in the magnetic field to obtain indications with respect to possible structural imperfections present on the walls of the pipeline.

14. The pipeline inspection gauge according to claim 1, wherein the pipeline inspection gauge is used for monitoring the structural integrity of a pipeline destined for transporting hydrocarbons.

15. A pipeline inspection gauge for monitoring the structural integrity of a pipeline, the pipeline inspection gauge being adapted to be inserted in a pipeline and to move along the pipeline, wherein the pipeline inspection gauge is adapted, during a monitoring operation, to generate a magnetic field which is conveyed to the wall of the pipeline and to reveal variations in the magnetic field using a sensor system, the pipeline inspection gauge comprising:
a central electromagnetic device adapted to generate a magnetic field;
a first magnetic conveyor connected to said central electromagnetic device suitable for conveying the magnetic field generated by the central electromagnetic device to the wall of the pipeline;
a second magnetic conveyor connected to said central electromagnetic device suitable for facilitating the closing of a magnetic circuit, conveying the magnetic field from the wall of the pipeline towards the central electromagnetic device;
at least one sensor system for revealing the magnetic field;
electric means for powering the pipeline inspection gauge and acquiring and storing data relating to the magnetic field detected;
wherein said central electromagnetic device comprises a bundle of metallic wires which opens at the two ends into multiple sub-bundles of wires, said sub-bundles of wires are included in said first and second magnetic conveyor and extend until they touch the internal wall of the pipeline, wherein said bundle of metallic wires are held together by said polymeric material adapted to degrade following prolonged contact with a mixture of hydrocarbons which results in separation of said bundle of metallic wires and loss of the generated magnetic field.

16. The pipeline inspection gauge according to claim 15, wherein said bundle of metallic wires is enveloped by a solenoid which, when subjected to an electric current, generates a magnetic field which passes through said bundle of wires and said sub-bundles of wires until it reaches the internal wall of the pipeline.

17. The pipeline inspection gauge according to claim 16, wherein said bundle of wires, said sub-bundles of wires and said solenoid are contained in a sheath made of said polymeric material suitable for degrading following prolonged contact with a mixture of hydrocarbons.

18. A pipeline inspection gauge for monitoring the structural integrity of a pipeline, comprising:
a central electromagnetic device adapted to generate a magnetic field, wherein said central electromagnetic device includes a plurality of divided elements made of a ferromagnetic material that are each a smaller size than said central electromagnetic device, wherein said divided elements are held together by a casing made of polymeric material adapted to degrade following prolonged contact with a mixture of hydrocarbons which results in separation of said divided elements and loss of the generated magnetic field;
a solenoid that envelops said divided elements which, when subjected to an electric current, generates the magnetic field which passes through said divided elements longitudinally;
a first magnetic conveyor extending as an arch between said central electromagnetic device and into contact with the wall of the pipeline, said first magnetic conveyor being adapted to convey the magnetic field generated by the central electromagnetic device to the wall of the pipeline, wherein said first magnetic conveyor comprises a flexible core made of ferromagnetic material in its interior and flexible polymeric material that contains said core suitable for degrading following prolonged contact with a mixture of hydrocarbons;
a second magnetic conveyor extending as an arch between said central electromagnetic device and into contact with the wall of the pipeline, said second magnetic conveyor being adapted to facilitate the closing of a magnetic circuit, conveying the magnetic field from the wall of the pipeline towards the central electromagnetic device, wherein said second magnetic conveyor comprises a flexible core made of ferromagnetic material in its interior and flexible polymeric material that contains said core suitable for degrading following prolonged contact with a mixture of hydrocarbons;

at least one sensor system for revealing the magnetic field;

an electronic device adapted to power the pipeline inspection gauge and to acquire and store data relating to the magnetic field detected;

wherein the at least one said sensor system and said electronic device, during a monitoring operation, reveal variations in the magnetic field indicative of the structural integrity of the pipeline;

wherein the pipeline inspection gauge is adapted to be inserted in a pipeline and to move along the pipeline.

* * * * *